(12) United States Patent
Suwa (10) Patent No.: US 12,121,212 B2
(45) Date of Patent: Oct. 22, 2024

(54) INSERTION INSTRUMENT, DISTAL END PORTION OF INSERTION INSTRUMENT AND MANUFACTURING METHOD OF INSERTION INSTRUMENT

(71) Applicant: OLYMPUS MEDICAL SYSTEMS CORP., Tokyo (JP)

(72) Inventor: Takahiro Suwa, Hachioji (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 58 days.

(21) Appl. No.: 17/592,729

(22) Filed: Feb. 4, 2022

(65) Prior Publication Data

US 2023/0248216 A1     Aug. 10, 2023

(51) Int. Cl.
| | |
|---|---|
| *A61B 1/00* | (2006.01) |
| *A61B 1/05* | (2006.01) |
| *A61B 1/06* | (2006.01) |
| *A61B 1/07* | (2006.01) |

(52) U.S. Cl.
CPC ........ *A61B 1/00096* (2013.01); *A61B 1/0011* (2013.01); *A61B 1/00147* (2013.01); *A61B 1/051* (2013.01); *A61B 1/0684* (2013.01); *A61B 1/07* (2013.01)

(58) Field of Classification Search
CPC .............. A61B 1/0008; A61B 1/00096; A61B 1/00147; A61B 1/0011; A61B 1/051; A61B 1/07; A61B 1/0684
See application file for complete search history.

(56) References Cited

U.S. PATENT DOCUMENTS

| | | | | |
|---|---|---|---|---|
| 4,741,327 A | * | 5/1988 | Yabe | A61B 1/0615 600/130 |
| 5,325,847 A | * | 7/1994 | Matsuno | A61B 1/00177 600/109 |
| 7,201,717 B2 | * | 4/2007 | Matsuura | A61B 1/05 600/110 |
| 2005/0267328 A1 | * | 12/2005 | Blumzvig | G02B 13/0065 348/E5.029 |
| 2008/0132760 A1 | * | 6/2008 | Takeuchi | A61B 1/0008 600/129 |
| 2009/0012358 A1 | * | 1/2009 | Ichihashi | A61B 1/00108 600/110 |
| 2009/0043166 A1 | * | 2/2009 | Ishii | A61B 1/00179 600/130 |

(Continued)

FOREIGN PATENT DOCUMENTS

| | | | |
|---|---|---|---|
| JP | 62-086323 A | | 4/1987 |
| JP | 2004008638 A | * | 1/2004 |

(Continued)

*Primary Examiner* — John P Leubecker
(74) *Attorney, Agent, or Firm* — Scully, Scott, Murphy & Presser, P.C.

(57) ABSTRACT

An insertion instrument includes: a holding member at a distal end of an insertion portion; a first hole formed in the holding member; a second hole that is formed in the holding member and that communicates with the first hole; a long member that is mounted to the holding member and that includes a distal end part and a main body portion; a partitioning member configured to narrow a space in which the main body portion is arranged; and a filler filling a gap around the long member.

19 Claims, 8 Drawing Sheets

(56) References Cited

U.S. PATENT DOCUMENTS

| | | | | |
|---|---|---|---|---|
| 2012/0206583 | A1* | 8/2012 | Hoshi | A61B 1/042 348/76 |
| 2013/0131453 | A1* | 5/2013 | Imai | A61B 1/00114 600/156 |
| 2013/0182099 | A1* | 7/2013 | Nakamura | G02B 6/4202 348/86 |
| 2014/0135577 | A1* | 5/2014 | Baumann | A61B 1/00179 600/109 |
| 2015/0265142 | A1* | 9/2015 | Ogawa | G02B 23/2476 600/109 |
| 2019/0117200 | A1* | 4/2019 | Morimoto | A61B 1/273 |
| 2020/0100663 | A1* | 4/2020 | Jensen | A61B 1/00096 |
| 2020/0237194 | A1* | 7/2020 | Kawahara | A61B 1/05 |
| 2022/0151480 | A1* | 5/2022 | Hansen | A61B 1/00165 |

FOREIGN PATENT DOCUMENTS

| | | | |
|---|---|---|---|
| JP | 2006020726 A | * | 1/2006 |
| JP | 2020116044 A | * | 8/2020 |

* cited by examiner

INSERTION INSTRUMENT, DISTAL END PORTION OF INSERTION INSTRUMENT AND MANUFACTURING METHOD OF INSERTION INSTRUMENT

BACKGROUND OF THE INVENTION

1. Field of the Invention

The present invention relates to an insertion instrument including a long member, such as an image pickup unit, disposed in a distal end portion of an insertion portion, a distal end portion of an insertion instrument and a manufacturing method of an insertion instrument.

2. Description of Related Art

Conventionally, insertion instruments used in the medical field or the industrial field have been known. In each of insertion instruments of recent years, long members, such as an image pickup unit and an illumination member, are incorporated in a distal end portion of an insertion portion.

With regard to such insertion instruments, for example, Japanese Patent Application Laid-Open Publication No. 2020-116044 discloses an oblique-viewing endoscope with an image pickup unit fixed to a distal end portion. Moreover, for example, Japanese Patent Application Laid-Open Publication No. 62-86323 discloses a side-viewing endoscope with a light guide, which is an illumination member, fixed to a distal end portion via application of an adhesive to the light guide. Furthermore, for example, Japanese Patent Application Laid-Open Publication No. 2004-8638 discloses a side-viewing endoscope with a large gap provided around a light guide, which is an illumination member.

SUMMARY OF THE INVENTION

An insertion instrument according to an aspect of the present invention includes: an insertion portion configured to be inserted into a subject; a holding member provided at a distal end of the insertion portion; a first hole formed in the holding member, the first hole being formed along a longitudinal axis of the insertion portion; a second hole formed in the holding member, the second hole being formed on a distal end side of the first hole so as to communicate with the first hole in a direction intersecting the longitudinal axis; a long member mounted to the holding member; a main body portion included in the long member, the main body portion being arranged in the first hole, a distal end part included in the long member, the distal end part being arranged in the second hole; a partitioning member disposed in the first hole, the partitioning member being configured to narrow a space in which the main body portion is arranged; and a filler filling a gap around the long member in the space partitioned by the partitioning member.

A distal end portion of an insertion instrument according to an aspect of the present invention includes: a holding member provided at a distal end of an insertion portion configured to be inserted into a subject; a first hole formed in the holding member, the first hole being formed along a longitudinal axis of the insertion portion; a second hole formed in the holding member, the second hole being formed on a distal end side of the first hole so as to communicate with the first hole in a direction intersecting the longitudinal axis; a long member mounted to the holding member; a main body portion included in the long member, the main body portion being arranged in the first hole; a distal end part included in the long member, the distal end part being arranged in the second hole; a partitioning member disposed in the first hole, the partitioning member being configured to narrow a space in which the main body portion is arranged; and a filler filling a gap around the long member in the space partitioned by the partitioning member.

A manufacturing method of an insertion instrument according to an aspect of the present invention includes: inserting a long member from a first hole formed along a longitudinal axis of a frame member; inserting a distal end part of the long member in a second hole, the second hole being formed on a distal end side of the first hole so as to communicate with the first hole in a direction intersecting the longitudinal axis of the frame member; inserting a partitioning member into the first hole to narrow a space in the first hole in which the long member is arranged; and filling a gap around the long member in the space partitioned by the partitioning member, with a filler.

DETAILED DESCRIPTION OF PREFERRED EMBODIMENT

Generally, a distal end portion of an endoscope, which is an insertion instrument, is filled with a filler around long members such as an image pickup unit and an illumination unit. The filler is used as a material for fixing and reinforcing the distal end portion against movement of internal components or a pushing force from a distal end.

The filler needs to be removed at the time of repair in which maintenance, replacement or the like of the long members such as the image pickup unit and the illumination unit is performed.

However, when the long members such as the image pickup unit and the illumination unit are removed, if an amount of filler filled is large, work for removal of the filler takes much time. Therefore, a smaller amount of filler filled is desirable.

In other words, insertion instruments such as endoscopes have the problem of difficulty in removing a large amount of filler filled around long members such as an image pickup unit and an illumination unit mounted to a distal end portion when the distal end portion is disassembled to remove the long members for, e.g., maintenance or repair.

Therefore, an insertion instrument of the present embodiment is configured to enable enhancement in repairability when long members such as an image pickup unit and an illumination unit are removed at the time of maintenance or repair, by reduction of a filler fixing the long members to a distal end portion.

An embodiment of an insertion instrument according to an aspect of the present invention will be described below with reference to the drawings. Note that the below embodiment is not intended to limit a configuration of the present invention.

Moreover, an endoscope is described as an example of the insertion instrument of the below embodiment. An oblique-viewing endoscope is described as an example of the endoscope here from among ultrasound endoscopes. The insertion instrument is applicable to gastrointestinal endoscopes each including a flexible insertion portion to be inserted into an upper or lower digestive tract of a living body and also to various types of what are called flexible endoscopes and what are called rigid endoscopes to be used for surgery, the rigid endoscopes each including a rigid insertion portion.

Furthermore, the present invention is applicable to medical insertion instruments and also to, for example, insertion instruments such as industrial endoscopes. In other words, the present invention is a technique that is applicable to insertion instruments such as endoscopes in which long members such as an image pickup unit and an illumination member are mounted in a distal end portion of an insertion portion.

It should be noted that: in the below description, the drawings are schematic ones; and dimensional relationships, ratios and the like among the respective elements may be different from actual ones. Parts that are different in dimensional relationship or ratio depending on the drawings may be included in the drawings.

Embodiment

Figure 1:
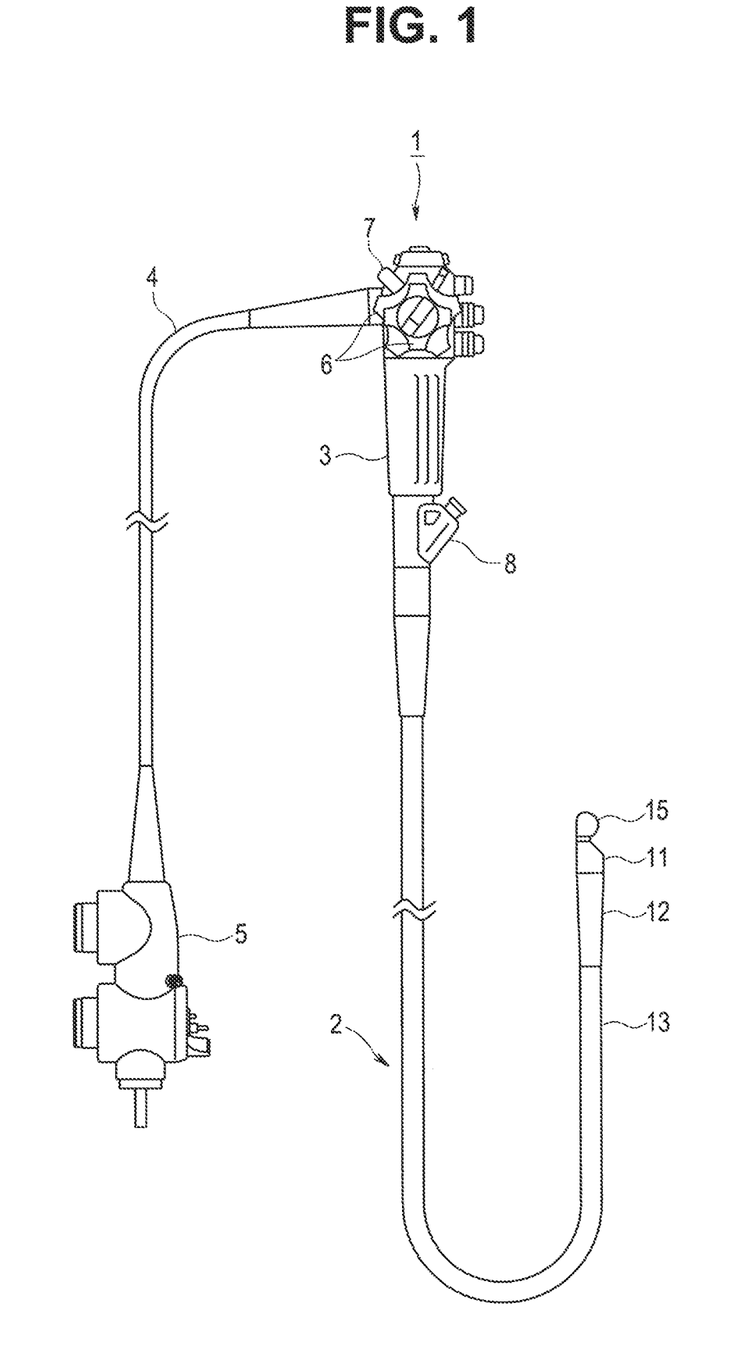
FIG. 1 is a schematic view illustrating a configuration of an endoscope according to an aspect of the present invention.

As illustrated in FIG. 1, an endoscope 1 of an insertion instrument of the present embodiment includes an insertion portion 2, an operation portion 3, a universal cord 4 and an endoscope connector 5.

The insertion portion 2, which includes long members such as an image pickup unit and an illumination unit disposed at a distal end, is configured to be inserted into a subject. The operation portion 3 is provided in such a manner as to be continuous with the proximal end side of the insertion portion 2. The universal cord 4 extends from a side portion of the operation portion 3. The endoscope connector 5 is provided in such a manner as to be continuous with the universal cord 4. The endoscope connector 5 is connected to, e.g., an observation apparatus configured to control the endoscope 1 and a light source apparatus configured to supply illuminating light to the endoscope 1.

The insertion portion 2 includes a distal end portion 11, a bending portion 12 and a flexible tube 13 in the order mentioned from the distal end side. The bending portion 12 is configured to be bendable according to an operation of a bending knob 6 provided at the operation portion 3. The flexible tube 13 has flexibility.

The flexible tube 13 of the insertion portion 2 is provided to be connected with the distal end side of the operation portion 3. An ultrasound transducer 15 is arranged at a distal end of the distal end portion 11 of the insertion portion 2. However, the endoscope 1 may be any of various endoscopes including no ultrasound transducer.

Figure 2:
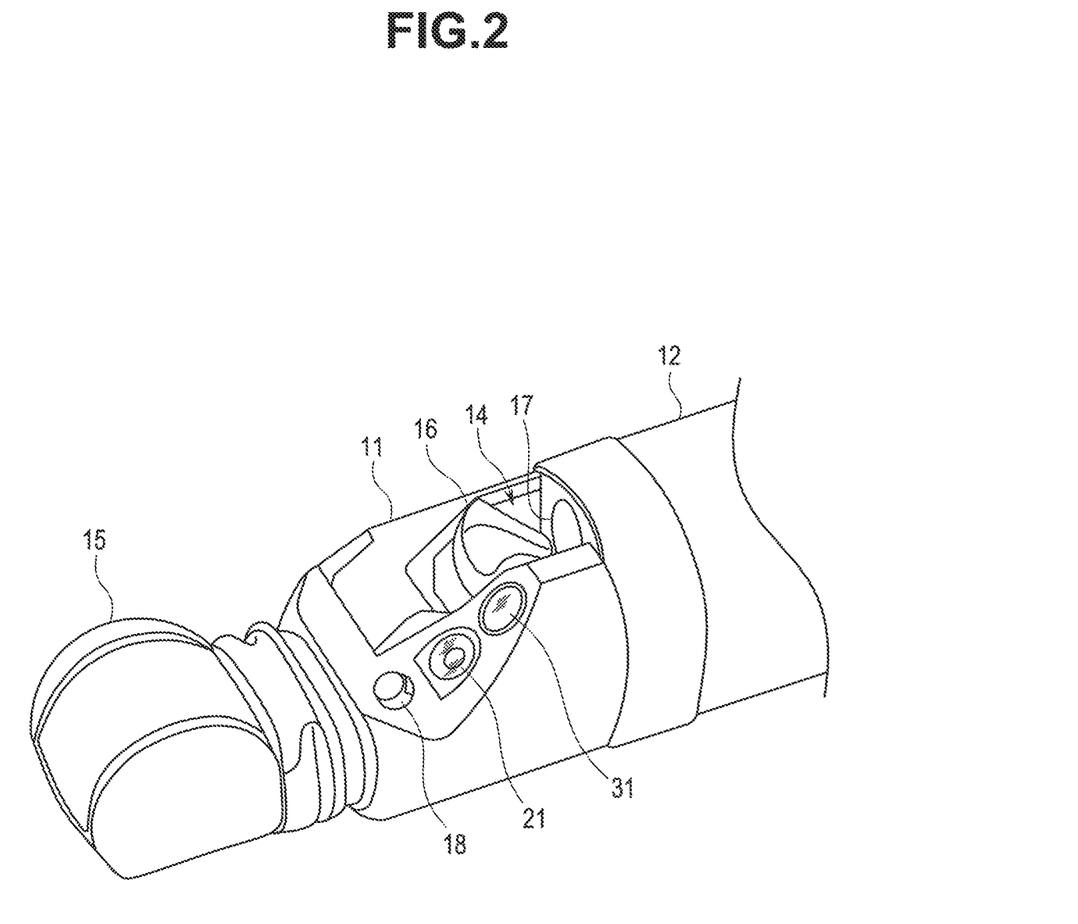
FIG. 2 is a perspective view illustrating a configuration of a distal end portion.

In the distal end portion 11, an opening 14 is provided, and a treatment instrument raising base (forceps elevator) 16 configured to change a direction in which, e.g., needle forceps, which are a treatment instrument, extend from the opening 14 is provided (see FIG. 2). Moreover, in the distal end portion 11, a treatment instrument channel opening 17 that communicates with the opening 14 is provided.

In the distal end portion 11, an observation window 21, an illumination window 31 and a gas/fluid feeding nozzle 18 are disposed in an inclined surface formed in a side portion of the opening 14. In other words, the endoscope 1 is an oblique-viewing endoscope, a direction of view of which is an obliquely forward direction. Note that the endoscope 1 may be a side-viewing endoscope, a direction of view of which is a sideward direction.

A forceps insertion port 8 for inserting, e.g., needle forceps, which are a treatment instrument, into a subject is provided in the operation portion 3. An operation lever 7 for operating the treatment instrument raising base 16 disposed in the distal end portion 11 is provided at the operation portion 3.

Inside the insertion portion 2, a treatment instrument channel is provided, and the forceps insertion port 8 is an insertion port of the treatment instrument channel. In other words, the endoscope 1 is an endoscope that enables insertion of a treatment instrument.

Here, a configuration of the distal end portion 11 of the insertion portion 2 of the present embodiment will be described below.

Figure 3:
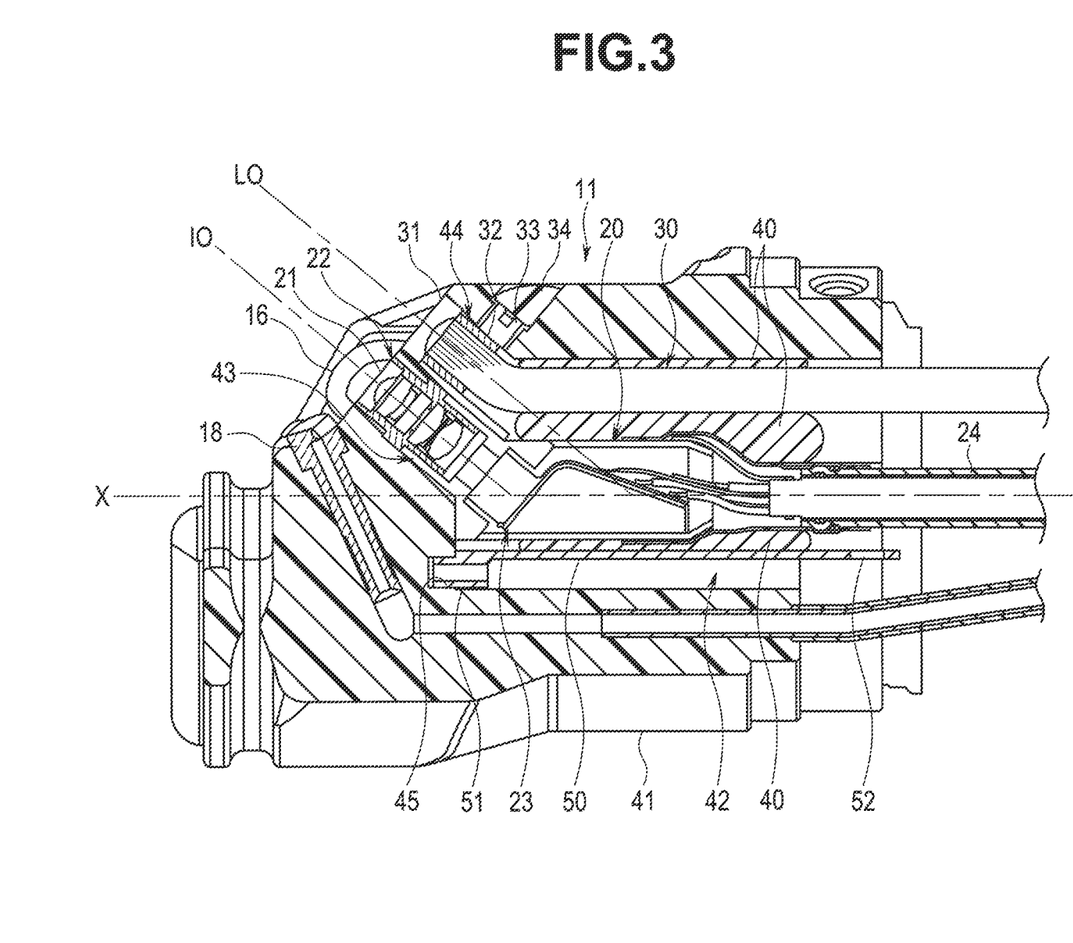
FIG. 3 is a sectional view illustrating the configuration of the distal end portion.

As illustrated in FIG. 3, the distal end portion 11 includes a distal end rigid portion 41 that serves as a holding member that is a frame member that holds, e.g., an image pickup unit 20, which is a long member, an illumination member 30, which is another long member, and the gas/fluid feeding nozzle 18.

The distal end rigid portion 41 is formed using a synthetic resin or metal. The distal end rigid portion 41 includes a first hole 42 formed in a direction along a longitudinal axis X of the insertion portion 2.

Moreover, the distal end rigid portion 41 further includes two second holes 43, 44 that communicate with the distal end side of the first hole 42 and that are formed along respective axes 10, LO extending in directions each intersecting with the longitudinal axis X at a predetermined angle.

In the distal end rigid portion 41, the image pickup unit 20 and the illumination member 30 are mounted in the first hole 42 and the second holes 43, 44. Furthermore, in the distal end rigid portion 41, a plate-like partitioning member 50 that partitions a first space of the first hole 42 into a second space 42a and a third space 42b is disposed in the vicinity of the image pickup unit 20 with a predetermined gap between the partitioning member 50 and the image pickup unit 20.

In the distal end rigid portion 41, the image pickup unit 20 and the illumination member 30 are disposed in the second space 42a formed by the first hole 42 partitioned by the partitioning member 50, and the second holes 43, 44. A gap around the image pickup unit 20 and the illumination member 30 in the second space 42a is filled with a filler 40, which is a fixing and reinforcing material such as an adhesive or a silicone-based material. In other words, in the second space 42a of the first hole 42, the second space 42a being partitioned by the partitioning member 50, the gap around the image pickup unit 20 and the illumination member 30 is filled with the filler 40 and the image pickup unit 20 and the illumination member 30 are fixedly attached to the distal end rigid portion 41.

The image pickup unit 20, which is an image pickup distal end portion, includes a lens unit 22 configuring a distal end part including an observation window 21, and an image pickup main body portion 23 in which an image pickup device, a substrate, etc., are mounted. An image pickup cable 24 extends from the image pickup unit 20.

Note that the lens unit 22 of the image pickup unit 20 protrudes at a predetermined angle from the image pickup main body portion 23. In the image pickup unit 20, the image pickup main body portion 23 is arranged in the first hole 42 and the lens unit 22 is inserted and arranged in the one second hole 43.

Here, the illumination member 30 is a light guide fiber bundle. A distal end portion of the illumination member 30 bends at a predetermined angle. The distal end portion of the illumination member 30 is inserted and fixed in a ring member 32 and inserted and arranged in the other second hole 44.

In this case, a distal end surface of the illumination member 30 is brought into abutment with a lens that serves as the illumination window 31 and the ring member 32 of the distal end portion is fixed to the distal end rigid portion 41 via a screw 33. A cover 34 for plugging up a screw hole is provided in the distal end rigid portion 41.

Figure 4:
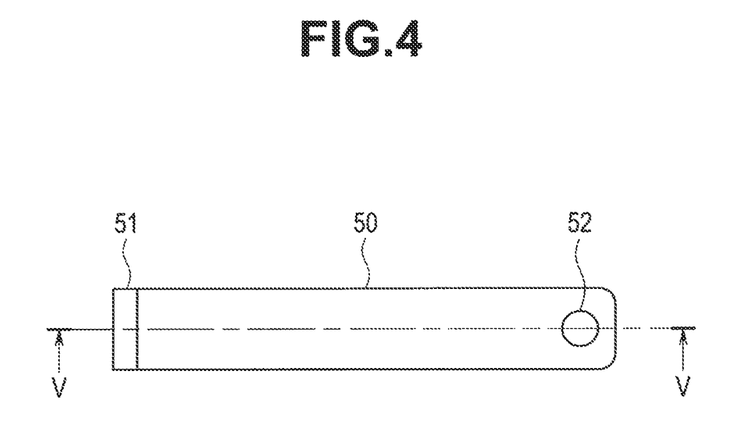
FIG. 4 is a plan view illustrating a configuration of a partitioning member.
Figure 5:
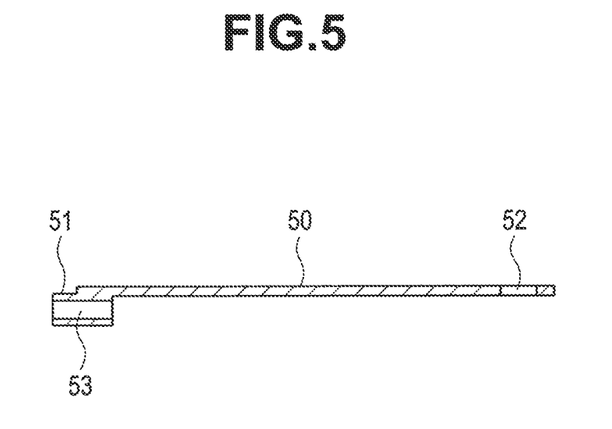
FIG. 5 is a sectional view illustrating the configuration of the partitioning member along line V-V in FIG. 4.

As illustrated in FIGS. 4 and 5, the partitioning member 50 includes a step-like fitting portion 51 at a distal end, and an engaging portion 52, which is a through hole, formed at a proximal end. In the fitting portion 51, a through hole 53 extending in a longitudinal direction is formed.

Note that a width dimension in a lateral direction orthogonal to the longitudinal direction of the partitioning member 50 is set so as to be substantially equal to a dimension in a width direction of the first hole 42 of the distal end rigid portion 41. Furthermore, the partitioning member 50 has such a length in the longitudinal direction that the proximal end protrudes rearward (toward the proximal end side) from a proximal end opening of the first hole 42 of the distal end rigid portion 41.

The partitioning member 50 is inserted in the first hole 42 of the distal end rigid portion 41. The fitting portion 51 at a distal end of the partitioning member 50 is fitted to a fitted portion 45 having a shape of a recess portion, the fitted portion 45 being formed in a wall surface on the distal end side, which forms the first hole 42 of the distal end rigid portion 41.

The engaging portion 52 of the partitioning member 50 is provided to, at the time of disassembling for maintenance or repair of, e.g., the image pickup unit 20 and the illumination member 30, allow a tool to engage with the engaging portion 52 to enable the partitioning member 50 to be easily pulled out from the distal end rigid portion 41.

Next, a method for manufacturing an endoscope 1, in which an image pickup unit 20 and an illumination member 30 are mounted to a distal end rigid portion 41 of a distal end portion 11 and a gap is filled with a filler 40, the gap being formed around the image pickup unit 20 and the illumination member 30, which are long members, by a partitioning member 50 being provided, will be described.

Figure 6:
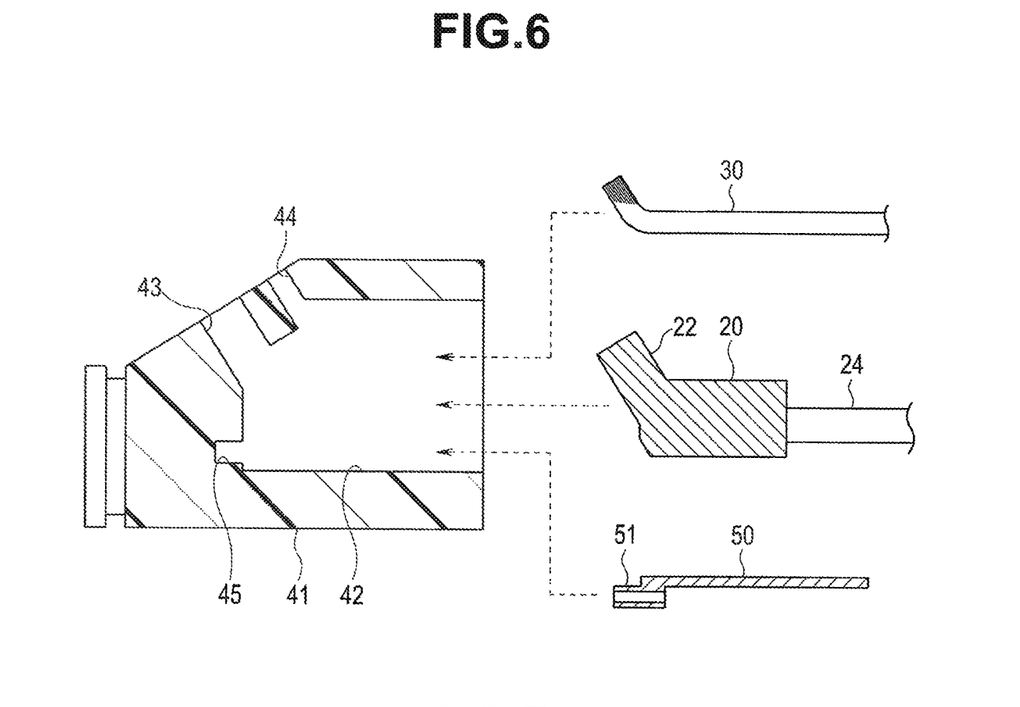
FIG. 6 is a sectional view illustrating a state before mounting of an image pickup unit, an illumination member and the partitioning member to a distal end rigid portion.

As illustrated in FIG. 6, an image pickup unit 20, an illumination member 30 and a partitioning member 50 are inserted into a first hole 42 of a distal end rigid portion 41, which is a holding member. At this time, the image pickup unit 20, the illumination member 30 and the partitioning member 50 may be mounted to the distal end rigid portion 41 in the order mentioned.

Figure 7:
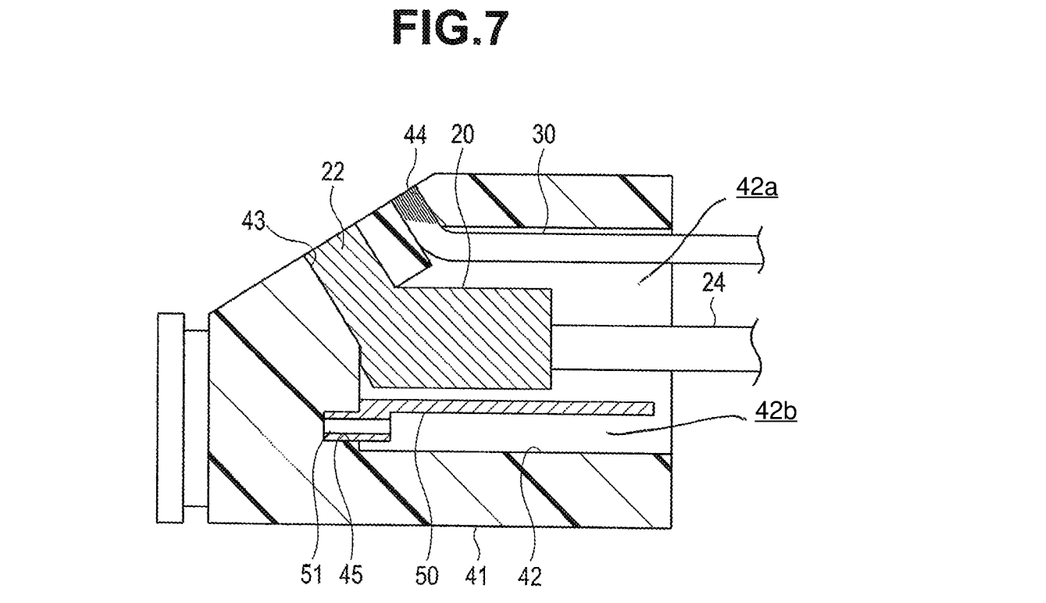
FIG. 7 is a sectional view illustrating a state in which the image pickup unit, the illumination member and the partitioning member are mounted to the distal end rigid portion.

The image pickup unit 20 is inserted from a proximal end opening of the first hole 42 of the distal end rigid portion 41, and as illustrated in FIG. 7, a lens unit 22 on the distal end side is inserted into the one second hole 43 and the image pickup main body portion 23 is arranged in the first hole 42.

The illumination member 30 is inserted from the proximal end opening of the first hole 42 of the distal end rigid portion 41 and a distal end part of the illumination member 30 is inserted in the other second hole 44.

The partitioning member 50 is inserted from the proximal end opening of the first hole 42 of the distal end rigid portion 41 and a fitting portion 51 at the distal end of the partitioning member 50 is fitted to a fitted portion 45.

In the distal end rigid portion 41, a space of the first hole 42 in which the image pickup unit 20 and the illumination member 30 are disposed can be narrowed by the partitioning member 50.

Figure 8:
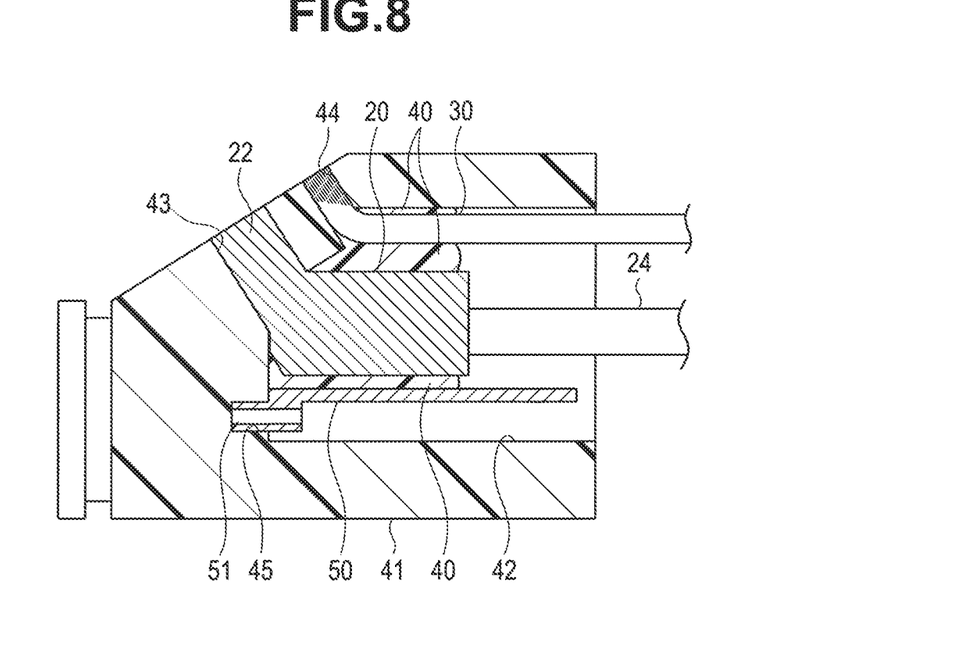
FIG. 8 is a sectional view illustrating a state in which the distal end rigid portion is filled with a filler.

Then, in the first hole 42 of the distal end rigid portion 41, as illustrated in FIG. 8, a gap around the image pickup unit 20 and the illumination member 30, the gap being narrowed by extra space being partitioned off by the partitioning member 50, is filled with a filler 40, which is a fixing and reinforcing member (packing material). Consequently, the image pickup unit 20 and the illumination member 30 are fixed to the distal end rigid portion 41 with a small amount of filler 40.

As described above, the endoscope 1 of the present embodiment can narrow a first space of the first hole 42 in which the long members such as the image pickup unit 20 and the illumination member 30 are mounted into a second space 42a and a third space 42b by providing the partitioning member 50 to the distal end rigid portion 41 which is a frame included in the distal end portion 11 and serves as a holding member, thus the filler 40 used when the image pickup unit 20 and the illumination member 30 are fixed can be reduced.

Consequently, in the endoscope 1, when, e.g., image pickup unit 20 and the illumination member 30 mounted in the distal end portion 11 are removed from the distal end rigid portion 41, the filler 40 can easily be removed. Therefore, the endoscope 1 enables enhancement in maintainability and repairability of, e.g., the image pickup unit 20 and the illumination member 30, which are internal components of the distal end portion 11.

According to the above description, the endoscope 1 enables reduction in amount of a filler, which is a fixing and reinforcing material for the image pickup unit 20 and the illumination member 30 incorporated in the distal end portion 11, and at the time of maintenance, or repair or replacement, of the image pickup unit 20 and the illumination member 30, work for removal of the filler 40 is easy.

(First Modification)

Figure 9:
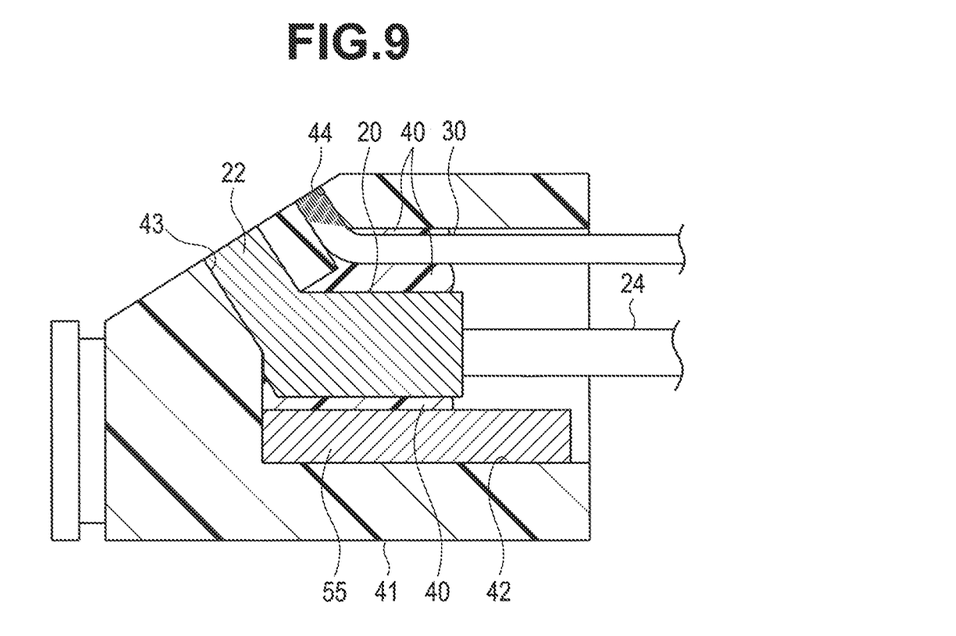
FIG. 9 is a sectional view of a distal end rigid portion according to a first modification, in which a thick block-like partitioning member is provided.

As illustrated in FIG. 9, instead of the thin plate-like partitioning member 50, a thick block-like partitioning member 55 may be employed.

(Second Modification)

Figure 10:
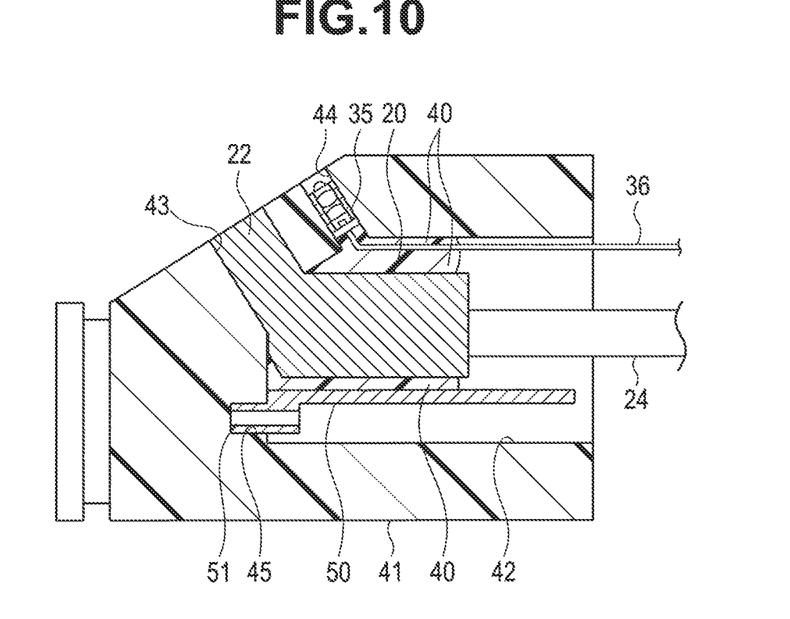
FIG. 10 is a sectional view of a distal end rigid portion according to a second modification, in which an illumination unit including an LED light source is provided.

As illustrated in FIG. 10, instead of the illumination member 30 that is a light guide fiber bundle, an illumination unit 35 that is an illumination member using a light-emitting element including an LED light source may be provided in the other second hole of a distal end rigid portion 41. Note that a cable 36 extends to the proximal end side from the illumination unit 35.

(Third Modification)

Figure 11:
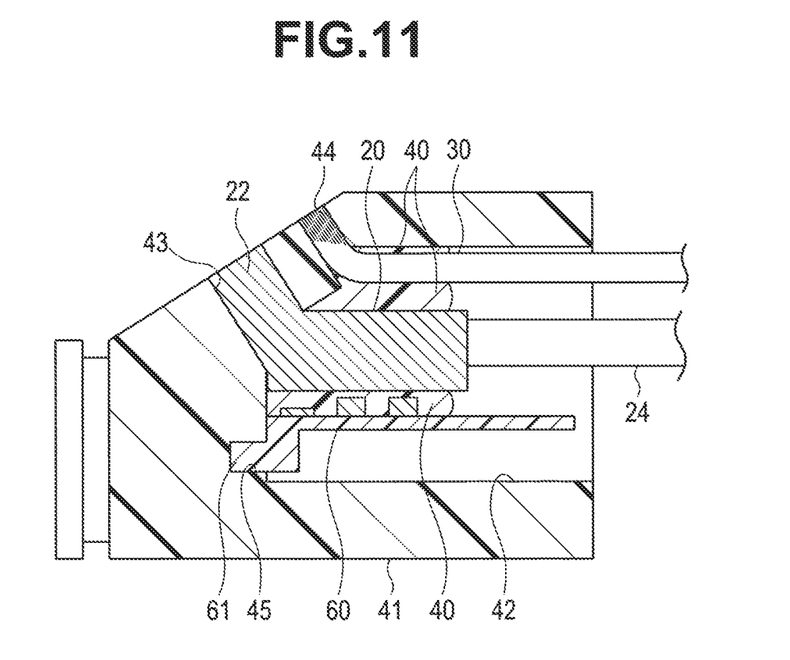
FIG. 11 is a sectional view of a distal end rigid portion according to a third modification, in which a substrate of an image pickup unit serves as a partitioning member.

As illustrated in FIG. 11, instead of the thin plate-like partitioning member 50, a circuit board 60 on which electronic components of an image pickup unit 20 are mounted may be used as a partitioning member. Note that the circuit board 60 is desirably of a rigid type and includes a fitting portion 61 at a distal end, the fitting portion 61 being fitted to a fitted portion 45 of a distal end rigid portion 41. Note that the circuit board 60 may be a circuit board of the LED light source in the illumination unit 35 of the second modification.

(Fourth Modification)

Figure 12:
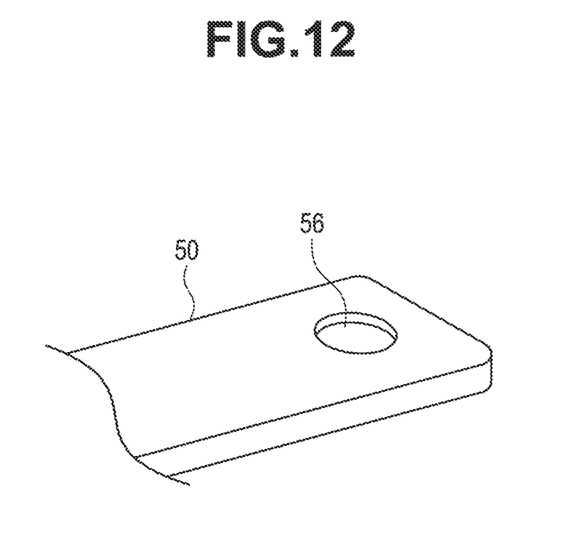
FIG. 12 is a perspective view partially illustrating an engaging portion according to a fourth modification, the engaging portion being provided in a partitioning member and being a bottomed hole.
Figure 13:
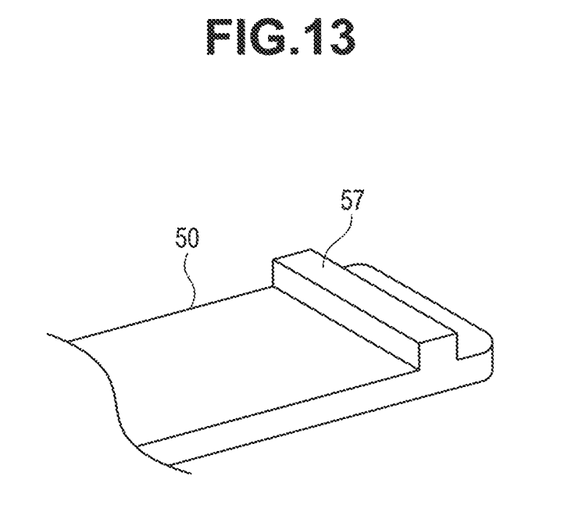
FIG. 13 is a perspective view partially illustrating an engaging portion according to the fourth modification, the engaging portion being provided at a partitioning member and being a projection portion.

Instead of the through hole, an engaging portion formed in a proximal end part of the partitioning member 50 may be a bottomed hole 56 as illustrated in FIG. 12 or a projection portion 57 as illustrated in FIG. 13.

Note that the above-described technique of the endoscope 1 is applicable to both reusable endoscopes and single-use endoscopes.

The invention described in the embodiment and modifications above is not limited to the embodiment and modifications, and in the practical phase, various modifications are possible without departing from the gist of the invention. Furthermore, the above embodiment and modifications include various phases of the invention, and various aspects of the invention may be extracted by arbitrary combinations of a plurality of elements disclosed.

For example, even if some elements are deleted from all the elements indicated in any of the above embodiment and modifications, a configuration with such elements deleted can be extracted as an aspect of the invention as long as such configuration can solve the stated problem and provide the stated effect.

What is claimed is:

1. An insertion instrument comprising:
an insertion portion configured to be inserted into a subject, the insertion portion comprising:
a distal end rigid body provided at a distal end of the insertion portion, the distal end rigid body comprising:
a first hole formed along a longitudinal axis of the distal end rigid body and defining a first space; and
a second hole formed on a distal end side of the first hole so as to communicate with the first hole, the second hole formed in a direction intersecting the longitudinal axis;
at least one of an illumination member and an image pickup unit mounted to the distal end rigid body, the at least one of the illumination member and the image pickup unit comprising:
a main body arranged in the first space; and
a distal end arranged in the second hole;
a partition disposed in the first space, the partition being a plate body configured to partition the first space into a second space and a third space, the main body is arranged in the second space, the partition comprising a projection configured to be engaged with the distal end rigid body; and
a filler filling a gap around the at least one of the illumination member and the image pickup unit only in the second space;
wherein a proximal end of the partition extends proximally from a proximal end face of the distal end rigid body.

2. The insertion instrument according to claim 1, wherein a third hole formed in the distal end rigid body, the projection of the partition is configured to be fitted to the third hole.

3. The insertion instrument according to claim 2, wherein the third hole is formed in a distal side surface of an inner surface of the first hole.

4. The insertion instrument according to claim 2, wherein a distal end surface of the projection abuts a bottom surface of the third hole.

5. The insertion instrument according to claim 1, wherein a proximal end of the partition protrudes proximally from a proximal opening of the first hole.

6. The insertion instrument according to claim 5, wherein the partition comprises one of a through hole or a bottomed hole at the proximal end of the partition.

7. The insertion instrument according to claim 1, wherein the partition comprises a circuit board of the image pickup unit.

8. The insertion instrument according to claim 7, wherein the circuit board comprises one or more electronic components disposed on a surface thereof and within the second space, the one or more electronic components being encased in the filler.

9. The insertion instrument according to claim 1, wherein the illumination member including a light-emitting element.

10. The insertion instrument according to claim 9, wherein the partition comprises a circuit board of the illumination member.

11. The insertion instrument according to claim 10, wherein the circuit board comprises one or more electronic components disposed on a surface thereof and within the second space, the one or more electronic components being encased in the filler.

12. The insertion instrument according to claim 1, wherein the distal end rigid body having an angled distal surface, a distal opening of the second hole is formed on the angled distal surface.

13. The insertion instrument according to claim 12, wherein the partition is disposed opposite the angled distal surface relative to the longitudinal axis.

14. The insertion instrument according to claim 1, wherein the partition has a rectangular cross-section in a direction perpendicular to the longitudinal axis.

15. The insertion instrument according to claim 1, wherein the projection of the partition comprises a through hole.

16. A distal end portion for use in an insertion portion of an insertion instrument, the distal end portion comprising:
a distal end rigid body provided at a distal end of the insertion portion, the distal end rigid body comprising:
a first hole formed along a longitudinal axis of the distal end rigid body and defining a first space; and
a second hole formed on a distal end side of the first hole so as to communicate with the first hole, the second hole formed in a direction intersecting the longitudinal axis;
at least one of an illumination member and an image pickup unit mounted to the distal end rigid body, the at least one of the illumination member and the image pickup unit comprising:

a main body arranged in the first space; and
a distal end arranged in the second hole;
a partition disposed in the first space, the partition being a plate body configured to partition the first space into a second space and a third space, the main body is arranged in the second space, the partition comprising a projection configured to be engaged with the distal end rigid body; and
a filler filling a gap around the at least one of the illumination member and the image pickup unit only in the second space;
wherein a proximal end of the partition extends proximally from a proximal end face of the distal end rigid body.

17. The distal end portion according to claim 16, wherein the distal end rigid body having an angled distal surface, a distal opening of the second hole is formed on the angled distal surface.

18. The distal end portion according to claim 17, wherein the partition is disposed opposite the angled distal surface relative to the longitudinal axis.

19. A manufacturing method of an insertion instrument, the manufacturing method comprising:

inserting at least one of an illumination member and an image pickup unit into a first hole formed along a longitudinal axis of a frame member, the first hole defining a first space;

inserting a distal end of the at least one of the illumination member and the image pickup unit into a second hole, the second hole being formed on a distal end side of the first hole so as to communicate with the first hole, the second hole formed in a direction intersecting the longitudinal axis;

inserting a partition into the first hole to partition the first space into a second space and a third space such that a proximal end of the partition extends proximally from a proximal end face of the distal end rigid body, the at least one of the illumination member and the image pickup unit is arranged in the second space; and filling around the at least one of the illumination member and the image pickup unit only in the second space with a filler.

* * * * *